(12) United States Patent
Myung et al.

(10) Patent No.: US 9,304,094 B2
(45) Date of Patent: Apr. 5, 2016

(54) METAL AND METAL OXIDE CO-FUNCTIONALIZED SINGLE-WALLED CARBON NANOTUBES FOR HIGH PERFORMANCE GAS SENSORS

(75) Inventors: Nosang Vincent Myung, Riverside, CA (US); Syed Mubeen, Santa Barbara, CA (US); Ashok Mulchandani, Riverside, CA (US); Marc Arnold Deshusses, Chapel Hill, NC (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 13/111,452

(22) Filed: May 19, 2011

(65) Prior Publication Data

US 2012/0080319 A1  Apr. 5, 2012

Related U.S. Application Data

(60) Provisional application No. 61/346,104, filed on May 19, 2010.

(51) Int. Cl.
*C25D 5/56* (2006.01)
*C25D 15/00* (2006.01)
*G01N 27/12* (2006.01)
*B82Y 15/00* (2011.01)

(52) U.S. Cl.
CPC .............. *G01N 27/127* (2013.01); *B82Y 15/00* (2013.01)

(58) Field of Classification Search
CPC ..................................... C25D 5/10; C25D 5/54
USPC ................... 427/205; 205/109, 170, 183, 198
See application file for complete search history.

(56) References Cited

U.S. PATENT DOCUMENTS

| 4,273,624 | A | * | 6/1981 | Laitinen et al. | 205/83 |
| 5,218,347 | A | * | 6/1993 | Deppe | 340/634 |
| 5,273,779 | A | | 12/1993 | Chen et al. | |
| 5,624,640 | A | | 4/1997 | Potthast et al. | |
| 6,134,946 | A | * | 10/2000 | Liu et al. | 73/31.06 |
| 2010/0089772 | A1 | | 4/2010 | Deshusses et al. | |

FOREIGN PATENT DOCUMENTS

WO   WO 2008153593 A1 * 12/2008 .............. H01L 21/00

OTHER PUBLICATIONS

Hsu et al., "Tin-Oxide-Coated Single-Walled Carbon Nanotube Bundles Supporting Platinum Electrocatalyst for Direct Ethanol Fuel Cell", Nanotechnology (no month, 2010), vol. 21, pp. 1-5.*
Star et al., "Gas Sensor Array Based on Metal-Decorated Carbon Nanotubes", J. Phys. Chem. B (no month, 2006), vol. 110, pp. 21014-21020.*

(Continued)

*Primary Examiner* — Edna Wong
(74) *Attorney, Agent, or Firm* — Buchanan Ingersoll & Rooney PC

(57) ABSTRACT

A method of co-functionalizing single-walled carbon nanotubes for gas sensors, which includes the steps of: fabricating single-walled carbon nanotube interconnects; synthesizing tin oxide onto the single-walled carbon nanotube interconnects; and synthesizing metal nanoparticles onto the tin oxide coated single-walled carbon nanotube interconnects.

21 Claims, 15 Drawing Sheets

(56) References Cited

OTHER PUBLICATIONS

Terranova et al., "Carbon Nanotubes for Gas Detection: Materials Preparation and Device Assembly," J. Phys.: Condens. Matter (no month, 2007), vol. 19, pp. 1-14.*

International Search Report and Written Opinion corresponding to PCT/US 2011/000896 issued on Aug. 24, 2011.

Extended European Search Report issued May 6, 2015 by the European Patent Office in corresponding European Patent Application No. 11783870.6.

Lu et al., "Room-Temperature Gas Sensing Based on Electron Transfer between Discrete Tin Oxide Nanocrystals and Multiwalled Carbon Nanotubes", Adv. Mater., vol. 21, No. 24, Jun. 2009, pp. 2487-2491.

* cited by examiner

METAL AND METAL OXIDE CO-FUNCTIONALIZED SINGLE-WALLED CARBON NANOTUBES FOR HIGH PERFORMANCE GAS SENSORS

CROSS-REFERENCE TO RELATED APPLICATION

This patent application claims benefit to U.S. Provisional Patent Application Ser. No. 61/346,104, filed May 19, 2010, which is incorporated herein by reference in its entirety.

GOVERNMENT INTEREST

This invention was made with Government support under Grant No. ES016026 awarded by the National Institutes of Health. The Government has certain rights in this invention.

FIELD OF THE INVENTION

This invention relates to a method of co-functionalizing single-walled carbon nanotubes (SWNTs) for gas sensors, and more particularly to a sensor having co-functionalized single-walled carbon nanotube interconnects formed by synthesizing tin oxide onto single-walled carbon nanotube interconnects, and synthesizing metal nanoparticles onto the tin oxide coated single-walled carbon nanotube interconnects.

BACKGROUND

The applications of $SnO_2$-SWNT (tin oxide-single-walled carbon nanotubes) hybrid structure as room temperature gas sensing platform has been demonstrated in previous studies. Combining efficient transduction property of SWNTs with high molecular detection property of $SnO_2$, excellent sensitivities to trace quantities of both oxidizing (limit of detection (LOD) of 25 ppb for $NO_2$) and reducing gases (LOD of 10 ppm for $H_2$) at room temperature was observed. The enhanced sensing performance observed for these hybrid nanostructures compared to unfunctionalized carboxylated SWNTs, is attributed to the availability of increased surface area of active elements, which can take part in gas molecule interactions. Although promising results were observed for these hybrid nanostructures, further improvement in sensitivity and particularly selectivity towards specific analytes remains a challenge.

Typically, sensors using $SnO_2$ as a sensory element use small amounts of additives such as Pd, Pt, Au, Ag, etc., to increase sensitivity and selectivity towards specific analytes. Generally, two different mechanisms have been considered to explain the observed enhancement in sensing performance for metal particles impregnated tin oxide sensors. The first is called chemical sensitization, where the metal particles catalytically activate the redox processes occurring at the tin oxide surfaces by lowering the activation energy for dissociation of analyte gases such as $O_2$, $H_2$, $H_2S$, CO, etc. The activated products then migrate towards the tin oxide surface, to react with adsorbed oxygen species resulting in a greater and faster degree of charge transfer between tin oxide and the adsorbate. The second mechanism is called electronic sensitization, where the metal nanoparticles interact electronically with the tin oxide surface forming charge depletion zones around the particles. Any changes observed in the work function of the additive due to gas adsorption and desorption will cause a change in the Schottky barrier between the metal particle and tin oxide resulting in conductivity changes. The two processes are schematically represented in FIG. 1.

SUMMARY

In accordance with an exemplary embodiment, a novel approach for high performance gas sensors using metal nanoparticles and $SnO_2$ co-functionalized single-walled carbon nanotubes has been developed. In an exemplary embodiment, a sequential electrochemical templating method was employed where SWNTs were first functionalized with tin oxide using electrochemical assisted approach, followed by electrodeposition of metal nanoparticles on top of $SnO_2$. Three different noble metal catalysts were selected for sensing studies such as palladium (Pd), platinum (Pt) and gold (Au). The sensors were tested towards different combustible and toxic gases ($NH_3$, $NO_2$, $H_2$, $H_2S$, water vapor) at room temperature. Among the fabricated sensors, Pd decorated $SnO_2$-SWNTs showed pronounced effects on introduction to target analytes with extremely high sensitive response obtained towards $H_2S$ (500% resistance change for 5 ppm). This remarkable improvement in sensing performance observed for Pd decorated $SnO_2$/SWNTs can be attributed to the formation of electro active elements on the surface of metal oxide-SWNT hybrid structures and enhanced catalytic decomposition of interacting gases on Pd nanoparticle surfaces.

In accordance with an exemplary embodiment, a method of co-functionalizing single-walled carbon nanotube interconnects for gas sensors comprises: fabricating single-walled carbon nanotube interconnects; synthesizing tin oxide onto the single-walled carbon nanotube interconnects; and synthesizing metal nanoparticles onto the tin oxide coated single-walled carbon nanotube interconnects.

In accordance with another exemplary embodiment, a sensor having co-functionalized single-walled carbon nanotube interconnects formed by synthesizing tin oxide onto the single-walled carbon nanotube interconnects, and synthesizing metal nanoparticles onto the tin oxide coated single-walled carbon nanotube interconnects.

In accordance with a further exemplary embodiment, a sensor comprises: a pair of microelectrodes; and a tin oxide coated single-walled carbon nanotube interconnects, which extends across a gap between the pair of microelectrodes, and wherein the tin oxide coated single-walled carbon nanotube interconnects include metal nanoparticles on top of the tin oxide coated single-walled carbon nanotubes.

The details of one or more embodiments of the disclosure are set forth in the accompanying drawings and the description below. Other features, objects, and advantages will be apparent from the description and drawings, and from the claims.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention. In the drawings.

DETAILED DESCRIPTION

Figure 1:
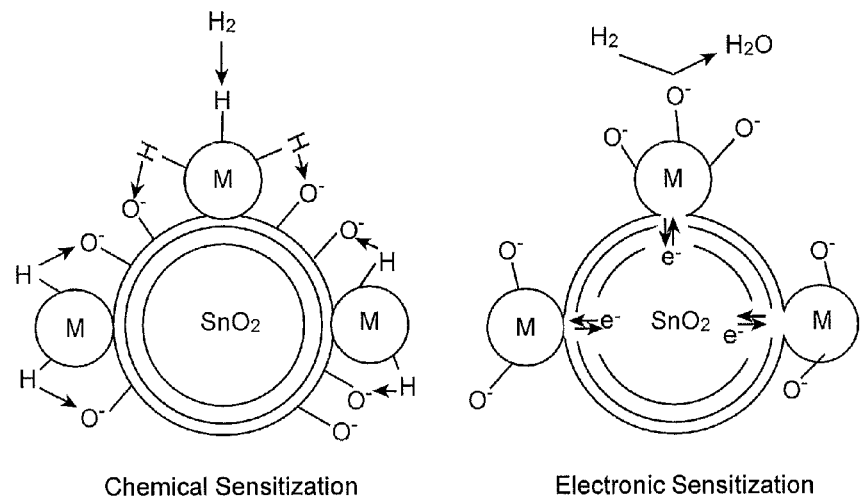
FIG. 1 is a schematic representation of chemical and electronic sensitization processes for noble-metal catalyst loaded $SnO_2$ gas sensor.

The synthesis of ternary hybrid nanostructures by electrodepositing metal nanoparticles on $SnO_2$-SWNT hybrid structure has been successfully demonstrated in accordance with an exemplary embodiment as set forth. In accordance with an exemplary embodiment, these nanostructures can be used as chemiresistors to compare the chemical sensing performance towards various analytes. Compared to $SnO_2$/SWNT hybrid nanostructures, Pd/$SnO_2$/SWNTs displays highly improved response towards all the analytes tested. Especially, Pd functionalized $SnO_2$/SWNT ternary nanostructures showed dramatic improvement in sensitivity for $H_2S$ gas. The dual role of Pd as a catalytic activator and Schottky barrier modulator may be attributed for the observed dramatic enhancement in sensitivity towards $H_2S$.

In accordance with an exemplary embodiment, experimental results are presented for $SnO_2$-SWNT gas sensors functionalized with different metal (Pd, Pt and Au) nanoparticles upon exposure to different analytes. The experimental results presented here are an excellent source for developing a reference response spectrum that can be later used to recognize a particular gas species.

It can be appreciated that in comparison with other techniques such as electron beam evaporation, self-assembly, sol-gel synthesis etc., electrodeposition offers a simple route to fabricate hetero nanostructures. Moreover, electrodeposition offers good control on the number and distribution of metal nanoparticles, which may be vital in tailoring the functionalities of such compound structures towards particular analytes.

Assembly of SWNTs:

In accordance with an exemplary embodiment, sensor arrays were microfabricated by the following methodology. Microelectrodes were patterned on $SiO_2$/Si substrates using photolithography followed by electron beam evaporation of Cr/Au electrodes. To fabricate SWNT interconnects across the electrodes; first, carboxylated-SWNTs (SWNT-COOH 80-90% purity) (Carbon Solution, Inc. Riverside, Calif., USA) were dispersed (10 μg/mL) in dimethyl formamide (DMF, Sigma Aldrich, MO, USA) using ultrasonic force for 60 min. Then, a 50 nano-liter of the SWNT solution was aligned between the gold electrodes using AC dielectrophoretic technique. AC dielectrophoresis (DEP) uses a non-uniform electric field, to align and to move the suspended nanotubes bundles towards the electrode. A 4 MHz ac field with 3 V peak to peak for 10 seconds was found to be optimal for alignment of SWNTs. Following alignment, the electrodes were rinsed with nanopure water and dried with nitrogen air. The sensors were then annealed at 300° C. for 60 minutes under reducing atmosphere (5% $H_2$+95% $N_2$) to minimize the contact resistance between the aligned SWNT network and the gold pads and to remove any DMF residues present. The number of SWNTs bridging the electrode gap was controlled by either adjusting the concentration of the SWNTs in the DMF solution or by adjusting the alignment time.

Synthesis of $SnO_2$ Coated SWNTs:

The electrolyte solution, for templating tin oxide on SWNTs was prepared according to the work of Min et al. (See Lai, M., et al., *Size-controlled electrochemical synthesis and properties of SnO2 nanotubes*. Nanotechnology, 2009. 20(18): p. 185602, which is incorporated herein in it entirety). First 100 mM of $NaNO_3$ (≥99.0%, Sigma-Aldrich, MO) is added to 75 mM of $HNO_3$ (70%, Sigma-Aldrich, MO) under constant stirring. 20 mM of $SnCl_2 5H_2O$ (≥98%, Sigma-Aldrich, MO) was then added, and the solution (pH of approximately 1.3) was aged for 12 hours under constant stirring prior to use. All depositions were carried out in potentiostatic mode (constant potential) at 25° C. Chronoamperometry measurements were carried out in a three electrode electrochemical setup using a commercial potentiostat (EG&G, Princeton Applied Research 263A Potentiostat/Galvanostat) with aligned SWNTs as working electrode and Pt wire (99.99%, Sigma-Aldrich, MO) and saturated Ag/AgCl wire as auxiliary and reference electrodes. Electrochemical cell was formed by dispensing a 3 μL of electrolyte solution on top of the aligned SWNT network and platinum and Ag/AgCl wires were positioned inside the droplet using micropositioner. After deposition process the electrodes were rinsed with deionized water to remove any metal salt residues and impurities present.

Synthesis of Metal Nanoparticles on $SnO_2$ Coated SWNTs:

Electrodeposition of metal nanoparticles on the $SnO_2$ coated SWNT networks were performed using a three electrode electrochemical cell configurations. For palladium deposition 10 g/L of Pd $(NH_2)_2(NO_2)_2$ and 100 g/L of ammonium sulfamate was first added. The solution pH was then adjusted to 8.0 by addition of sulfamic acid and sodium hydroxide. For gold and platinum deposition, commercially available ready-to-use electroplating solution from Technic Inc (CA) was used as electrolyte. All aqueous solutions were prepared using nanopure water. For all depositions, alkaline electrolyte solutions are selected (pH of approximately 7.5 to approximately 8.0) to prevent the dissolution of Cr adhesion layer which can be readily attacked in an acidic environment. In accordance with an exemplary embodiment, $SnO_2$ coated SWNTs served as working electrodes with Pt wire and Ag/AgCl wire as counter and reference electrodes respectively. High-resolution field emission scanning electron microscopy (FE-SEM) and energy dispersive x-ray spectroscopy (EDX) was used as a characterization tool for the deposited samples.

Gas Sensing Studies:

For gas sensing studies, the sensors were wire-bonded and each sensor was connected in series with a load resistor. A 3.6 $cm^3$ sealed glass chamber with gas inlet and outlet ports for gas flow-through was positioned over the sensor chip. All experiments were conducted with desired analyte gas (purity: 99.998%) diluted in dry air (purity: 99.998%) at a gas flow of 200 std. $cm^3$ $min^{-1}$. The analyte and dry air gas flow rates were regulated by mass flow controllers (Alicat Scientific Incorporated, Tucson, Ariz., USA). A custom Lab view computer program was developed to continuously control and monitor the voltage of the circuit using field point analog input and output modules (National Instruments, Austin, Tex., USA). In all the experiments, sensors were first exposed to air to obtain the baseline, then to a desired concentration of analyte gas, and then back to air, which completed one cycle. This process was repeated for different concentration of analyte being tested. All results shown here is a representation of 5 sensors or more.

Figure 2:
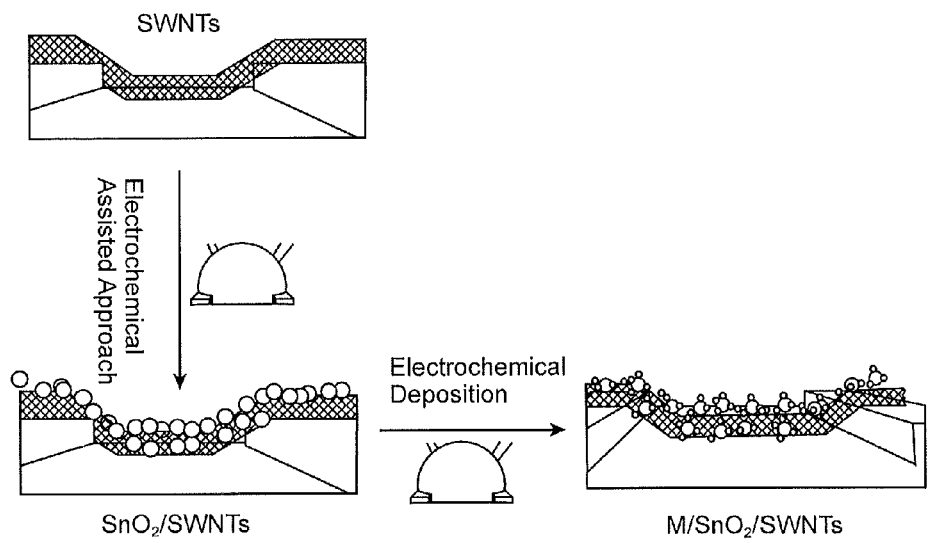
FIG. 2 is a schematic representation of sequential electrochemical templating approach for fabricating hetero-nanoarchitectures.

Nanobuilding Blocks using Sequential Templating Approach:

In order to construct hybrid/hetero nano-architectures for gas sensing applications, tin oxide coated SWNTs were first synthesized. As reported in previous studies, electrochemical assisted approach was used to template discrete tin oxide nanocrystallites on the surface of SWNTs. Aligned SWNTs between gold electrodes served as the working electrode. On applying a suitable cathodic potential (−0.4 V vs. Ag/AgCl wire), nitrate ions were reduced on the surface of SWNTs producing hydroxyl ions which increased the local pH initiating the chemical precipitation of tin oxy-hydroxide on SWNTs, which was later converted to tin oxide nanocrystallites during post annealing process. Palladium nanoparticles were then electrodeposited on the $SnO_2$-SWNT hybrid nanostructures. For Pd deposition, chronoamperometry technique with a constant deposition potential of −0.8 V vs. Ag/AgCl wire was used. The deposition charge was fixed to 5 µC. FIG. 2 shows a schematic representation of sequential electrochemical templating approach to form metal and metal oxide co-functionalized SWNTs.

Figure 3:
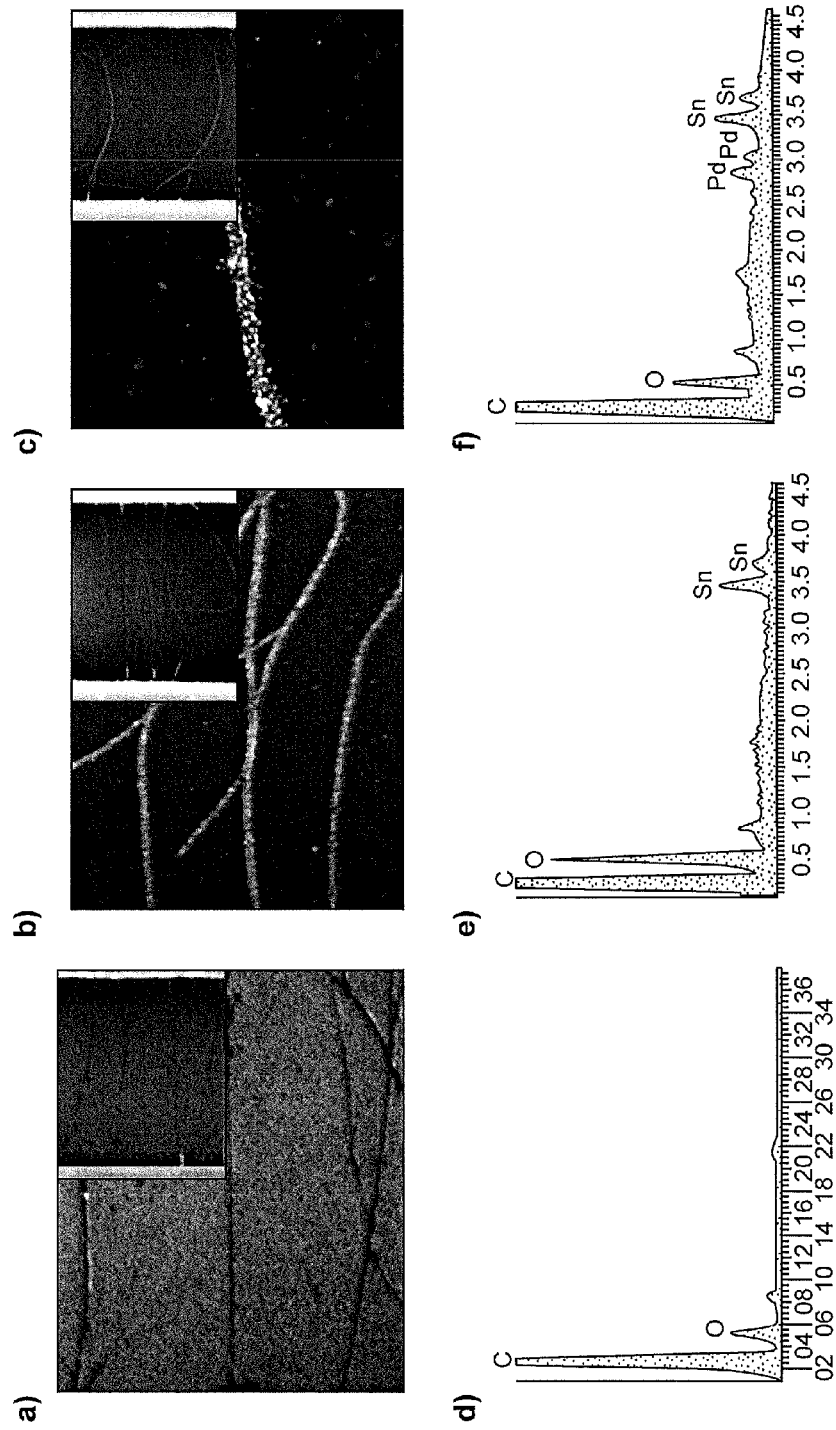
FIG. 3 are SEM images of a) carboxylated SWNTs, b) $SnO_2$ coated SWNTs and c) Pd nanoparticles decorated $SnO_2$/SWNT heterostructure, with their corresponding EDX spectrums (d-f), and with low SEM magnification images of the devices shown in the inset.

FIGS. 3a, 3b, and 3c show SEM images of carboxylated SWNTs, $SnO_2$ nano crystallites coated SWNTs and Pd nanoparticles decorated $SnO_2$-SWNT nanostructures, respectively. SEM observations (FIG. 3b) reveal that the tin oxide nanocrystallites are coated homogenously all along the surface of SWNTs. In addition to a homogenous surface observed for $SnO_2$-SWNTs, the nano-architectures consist of uniformly loaded palladium nanoparticles onto the surface of $SnO_2$-SWNTs (FIG. 3c) after electrodeposition of Pd. The EDX analysis (FIG. 3f) confirmed the presence of Pd, Sn, C and O, which substantiates that $SnO_2$-SWNT hybrid nanostructures have been successfully modified with Pd nanoparticles using sequential electrochemical templating approach. No corresponding peaks of Pd and Sn are observed for carboxylated SWNTs (FIG. 3d) and no Pd peak was observed for $SnO_2$ coated SWNTs (FIG. 3e).

Figure 4:
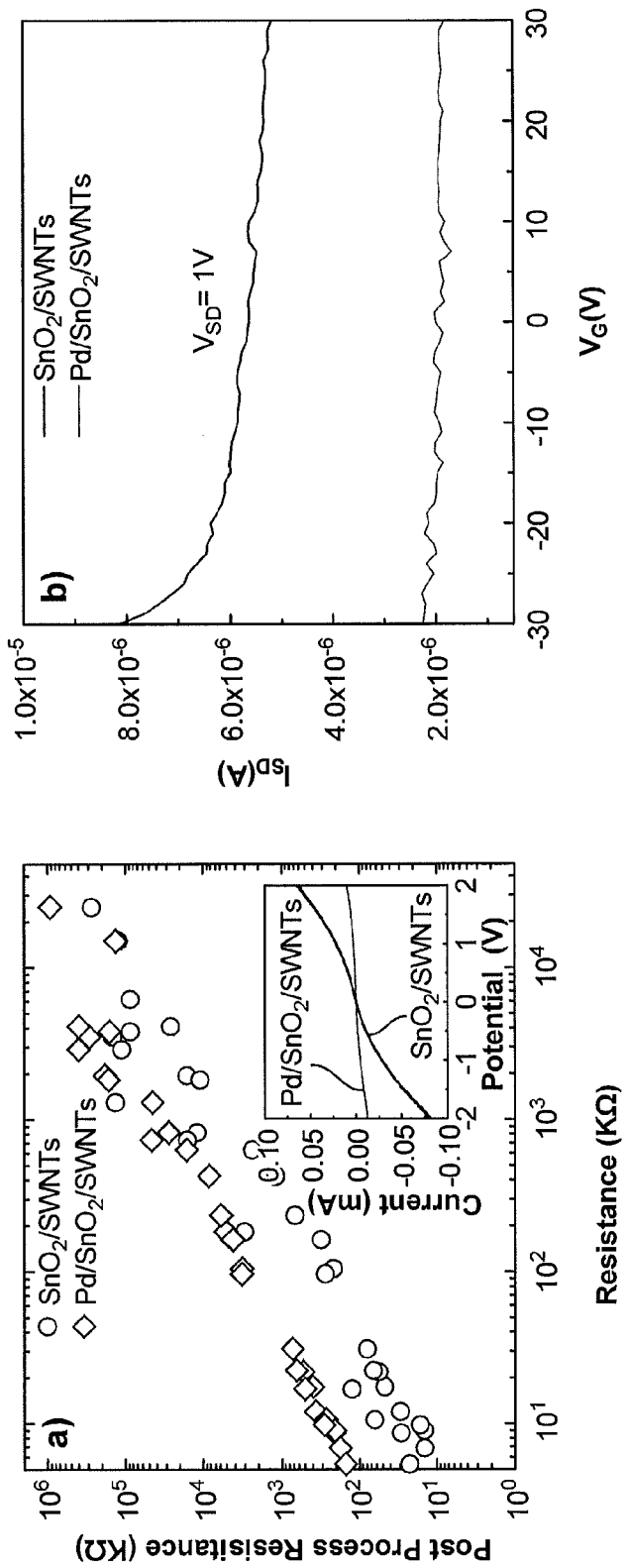
FIG. 4 is an image of a) resistance change observed after Pd nanoparticle decoration on $SnO_2$/SWNTs, and wherein device resistances after $SnO_2$ decoration varied from 5 Kohms to 10 Mohms, the inset shows corresponding I-V curve obtained for a single device, and b) FET measurements of $SnO_2$/SWNT device and Pd decorated $SnO_2$/SWNT device.

The electronic interaction between palladium nanoparticles and $SnO_2$-SWNT hybrid nanostructure was investigated using room temperature conductance and field effect transistor (FET) measurements (FIG. 4). It should be noted that all electrical transport measurements were done at ambient conditions. Two important electrical transport characteristics are observed for palladium decorated $SnO_2$-SWNT device. First, there is a dramatic decrease in conductance on palladium nanoparticle functionalization. FIG. 4a shows the change of resistance observed after Pd nanoparticle decoration on $SnO_2$/SWNT hybrid structure.

The initial resistances of the $SnO_2$/SWNT device were varied from 5 Kohms to 10 Mohms. For all resistance ranges, introduction of palladium nanoparticles increased the device resistance with a decrease in source-drain current observed for all gate voltages with no gate dependency (FIG. 4b).

Figure 5:
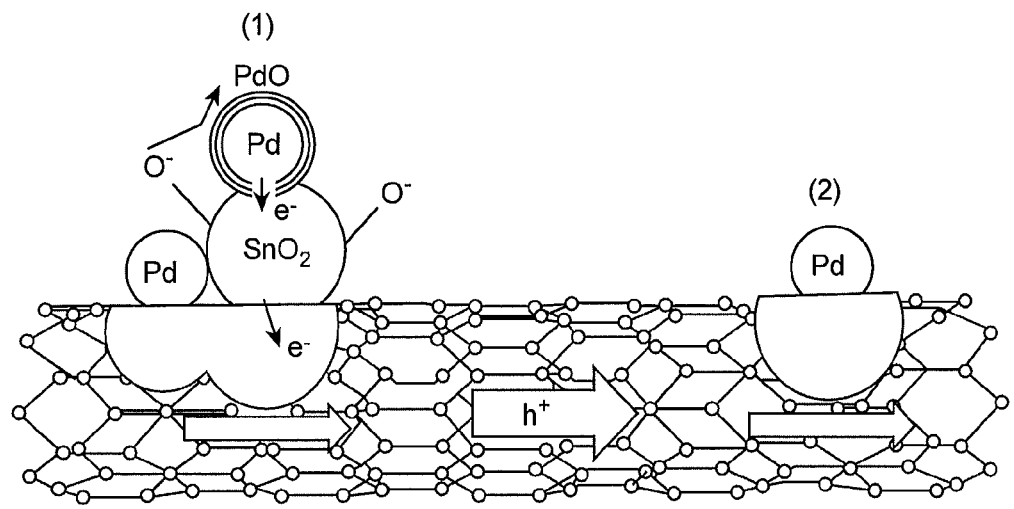
FIG. 5 are schematic depictions of the two major processes which may occur on Pd nanoparticle decoration on $SnO_2$/SWNT compound structure, wherein (1) shows oxidation of Pd to PdO by the ionosorbed oxygen species present on the tin oxide resulting in electron transfer across $SnO_2$/SWNT interface and (2) shows Pd nanoparticle deposition on SWNTs results in formation of a depletion region creating obstruction for hole transport and therefore decreases carrier mobility.

The increase in resistance after Pd nanoparticle deposition implies that there is a net electron transfer from palladium nanoparticles to the $SnO_2$-SWNT hybrid nanostructure device. As electrochemical assisted approach for templating tin oxide on SWNTs produces discrete tin oxide nanocrystallites, electrodeposition of palladium nanoparticles on both SWNT surface and on $SnO_2$ nanocrystallites deposited on SWNTs. The palladium nanoparticles decorated on surface of SWNTs act as charge scattering sites decreasing device mobility and hence conductivity as reported in our previous studies and also substantiated by our FET measurements. For palladium nanoparticles decorated on $SnO_2$ nanocrystallites, there could be rapid oxidation of palladium nanoparticles by ionosorbed oxygen species present on the surface of $SnO_2$. The oxidation of palladium results in a net electron transfer into the $SnO_2$ conduction band, which further results in electron transfer across $SnO_2$-SWNT interface, resulting in a decrease in conductance for p-type SWNTs. Hence, it can be appreciated that the main processes that produce the conductance changes are the removal of ionosorbed oxygen species by reaction with palladium nanoparticle adsorbate and creation of nano-Schottky barriers associated with palladium nanoparticle formation on SWNT surface. The two processes are schematically represented in FIG. 5.

Figure 6:
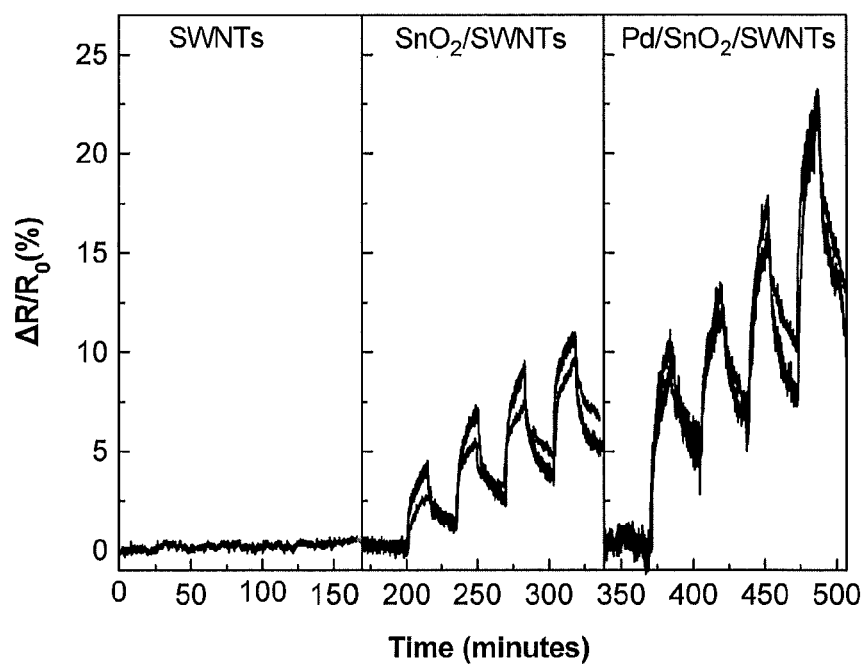
FIG. 6 is a sensor response of SWNTs, $SnO_2$/SWNTs and Pd/$SnO_2$/SWNTs towards different concentration pulses of $H_2$ (10, 50, 100 and 250 ppm).

Gas Sensors Constructed with Pd/$SnO_2$/SWNTs Nanoarchitectures:

The sensing performance of SWNTs, $SnO_2$/SWNTs and Pd/$SnO_2$/SWNTs towards different hydrogen concentration pulses are shown in FIG. 6. Functionalizing the SWNT surface with $SnO_2$ nanocrystallites enhances the sensing performance towards trace quantities of hydrogen concentration (limit of detection (LOD)—10 ppm). However, functionalizing these hybrid nanostructures with Pd leads to an enhancement in sensor performance (which is evaluated as percentage change in resistance, $\Delta R/R0 = Rgas/Rair^{-1}$) almost double compared to $SnO_2$/SWNT samples.

The responses of Pd/$SnO_2$/SWNTs sensors (FIG. 7a) to all of the gases tested here are higher than those of sensors fabricated from carboxylated SWNTs and $SnO_2$ coated SWNTs. Most remarkable is that the palladium decorated $SnO_2$-SWNT hybrid structure showed very high sensitivity towards $H_2S$, even when the concentration of $H_2S$ (5 ppm) was lower than the concentrations of other analytes tested.

Figure 7:
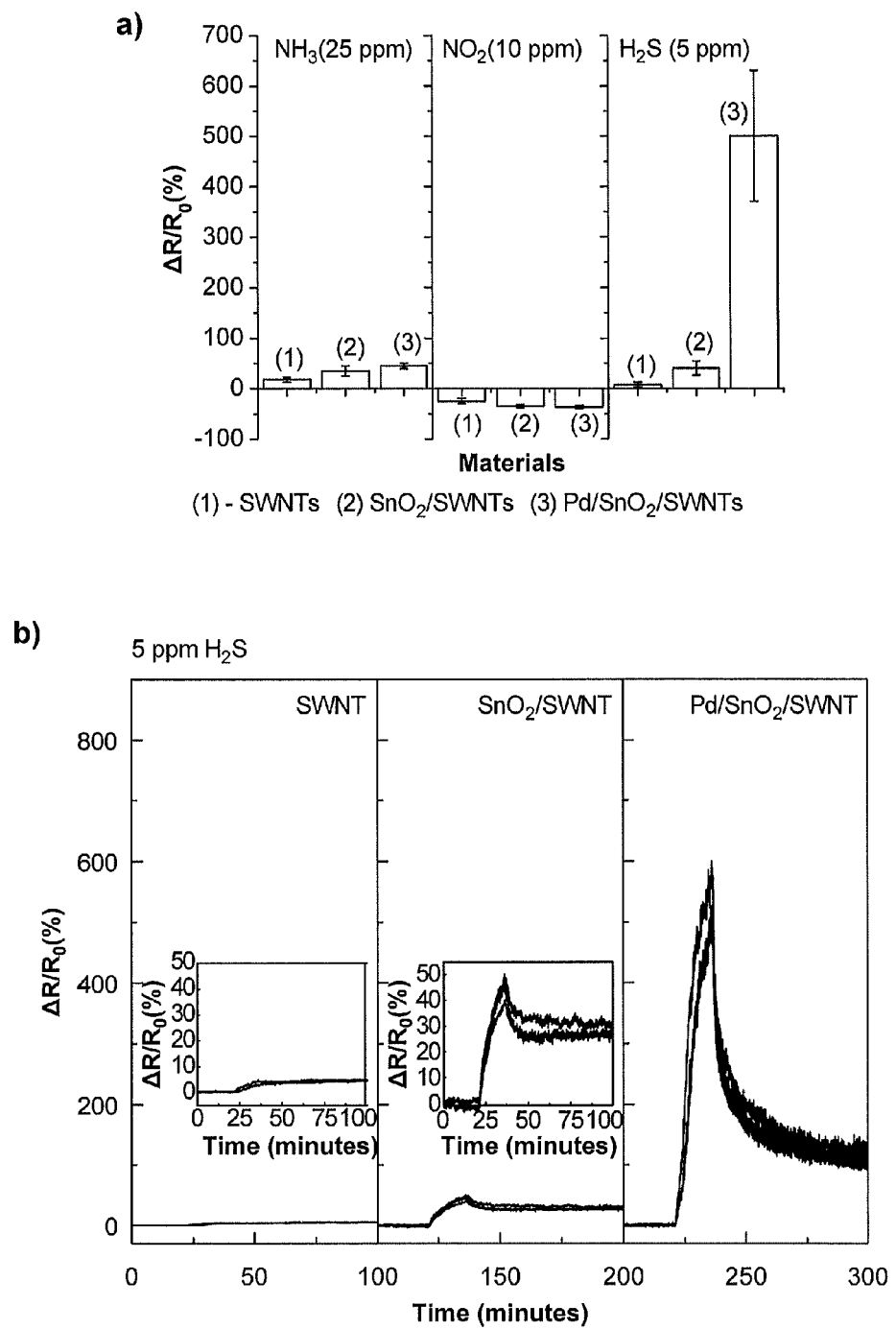
FIG. 7 are a) histogram showing sensor performance of SWNTs, $SnO_2$/SWNTs and Pd/$SnO_2$/SWNTs towards $NH_3$, $NO_2$ and $H_2S$, and b) real-time sensing response of SWNTs, $SnO_2$/SWNTs and Pd/$SnO_2$/SWNTs towards 5 ppm $H_2S$ concentration, and wherein the insets are magnified responses for SWNTs and $SnO_2$/SWNT sensors.

The sensing performance of all three nanoarchitectures used in this study towards 5 ppm $H_2S$ is shown in FIG. 7b.

For $H_2S$ gas, the sensing response of Pd/$SnO_2$/SWNT structure is around 600% for 5 ppm concentration, compared to 50% obtained for $SnO_2$/SWNTs and 5% obtained for carboxylated SWNTs. It can be appreciated that a response of this magnitude (600% for 5 ppm $H_2S$) observed for Pd/$SnO_2$/SWNT sensor at room temperature has not been reported elsewhere using any sensor element.

It can be appreciated that two processes are considered to explain the enhancement in sensing performance observed for palladium catalysts on tin oxide-SWNT sensors. The first process is called "electronic sensitization", where the metal catalyst added creates an energy barrier, which depends primarily on the work function of the metal catalysts used. As work function of palladium (5.15 eV) is higher than the $SnO_2$ (4.7 eV) and SWNTs (4.7-4.9 eV), a charge depletion zone is formed around the particles. Here the sensing performance attributed to the modulation of these nano-Schottky barriers on introduction of the analyte gas. The second process is called "chemical sensitization" where the catalytic activity of Pd nanoparticles is utilized. Here the enhancement is due to a "spill over" effect, in which the gas molecules dissociate on the catalytic palladium particles and then diffuse across and/or through the particles reaching the $SnO_2$ surface resulting in conductance change. Considering the improvement observed at room temperature operation, the enhanced sensing performance observed for Pd/$SnO_2$/SWNT $H_2S$ gas sensor can be attributed to both the processes mentioned above. Hence, the significant decrease in conductance resulted from: 1) modulation of the nano-Schottky barriers due to the changes in the work function of the palladium nanoparticles on introduction of $H_2S$ gas. $H_2S$ gas can lower the work function of the palladium metal resulting in easy electron transfer from metal nanoparticle to SWNTs and/or to $SnO_2$ surface; and 2) palladium nanoparticles can lower the activation energy for decomposition of $H_2S$ gas which could facilitate the diffusion of activated products (H and SH) towards tin oxide surface. The activated products can then react with oxygen atoms on the tin oxide surface leaving behind oxygen vacancies, which serves as electron donors, hence decreasing device conductance.

Figure 8:
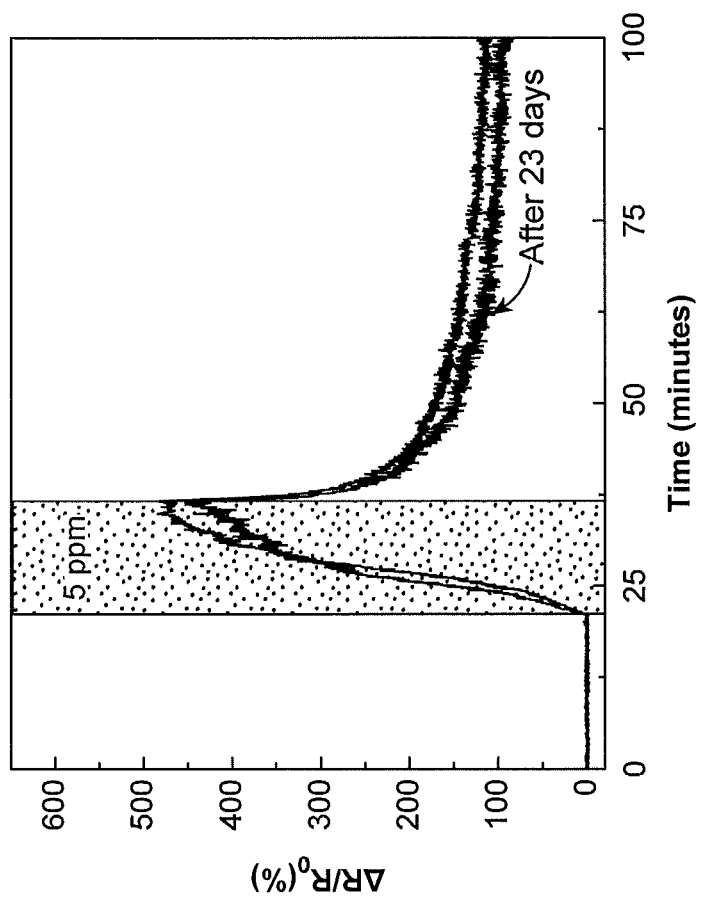
FIG. 8 is a comparison of sensing performance towards 5 ppm $H_2S$ gas for as fabricated Pd/$SnO_2$/SWNTs with that of same sensor after 23 days of storage.

Another important factor for evaluating nanosensor performance is the stability and reproducibility of the device. The stability of the Pd/$SnO_2$/SWNT sensor was examined by comparing its response to 5 ppm $H_2S$ obtained immediately after sensor fabrication to response obtained after 3 weeks. The sensors were stored in a dessicator in the corresponding time period. As illustrated in FIG. 8, the responses of the Pd/$SnO_2$/SWNT sensor showed no obvious degradation, suggesting its long-term stability and its potential for real time applications.

Figure 9:
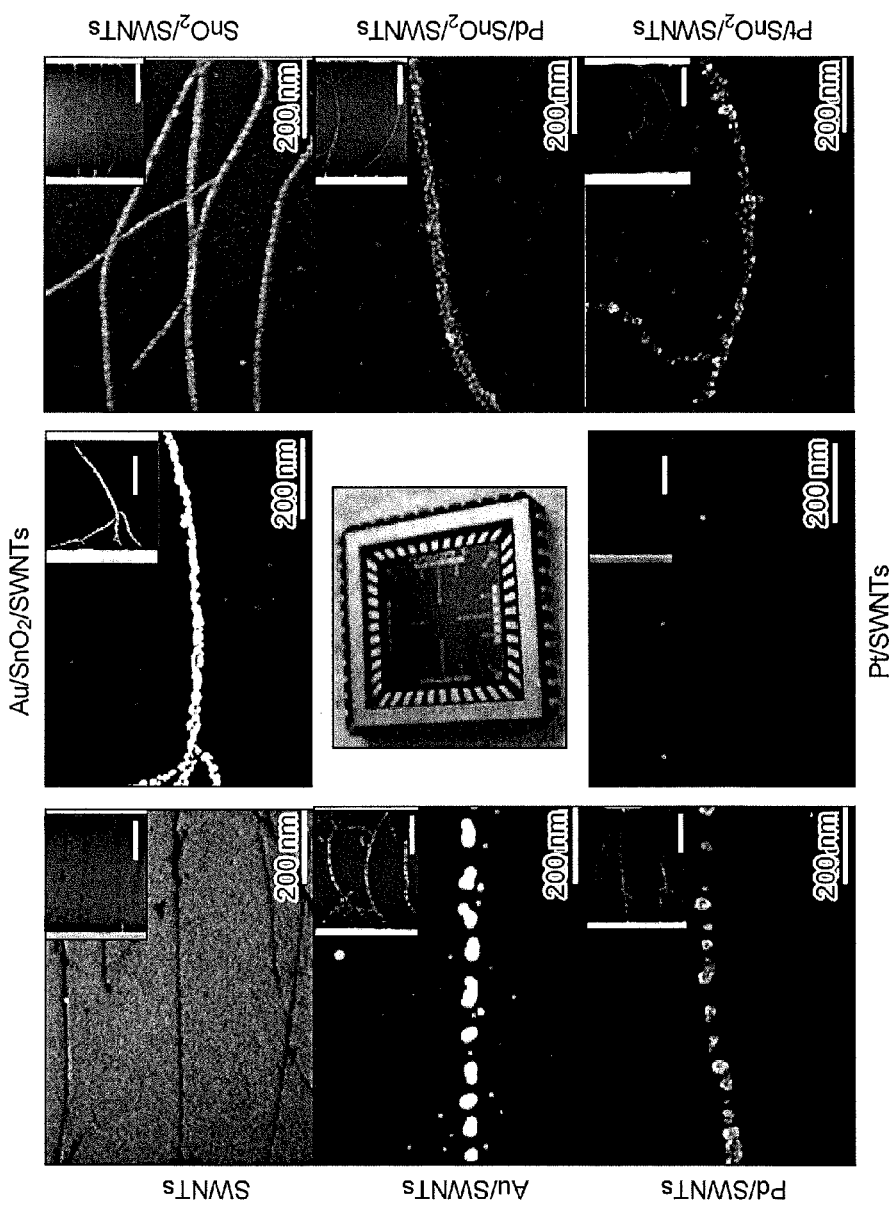
FIG. 9 is an optical and SEM images of a nano gas sensor array using SWNTs functionalized with different sensing elements, and wherein the inset shows low magnification SEM images of the same (all scale bars in the inset correspond to 1 μm).
Figure 10:
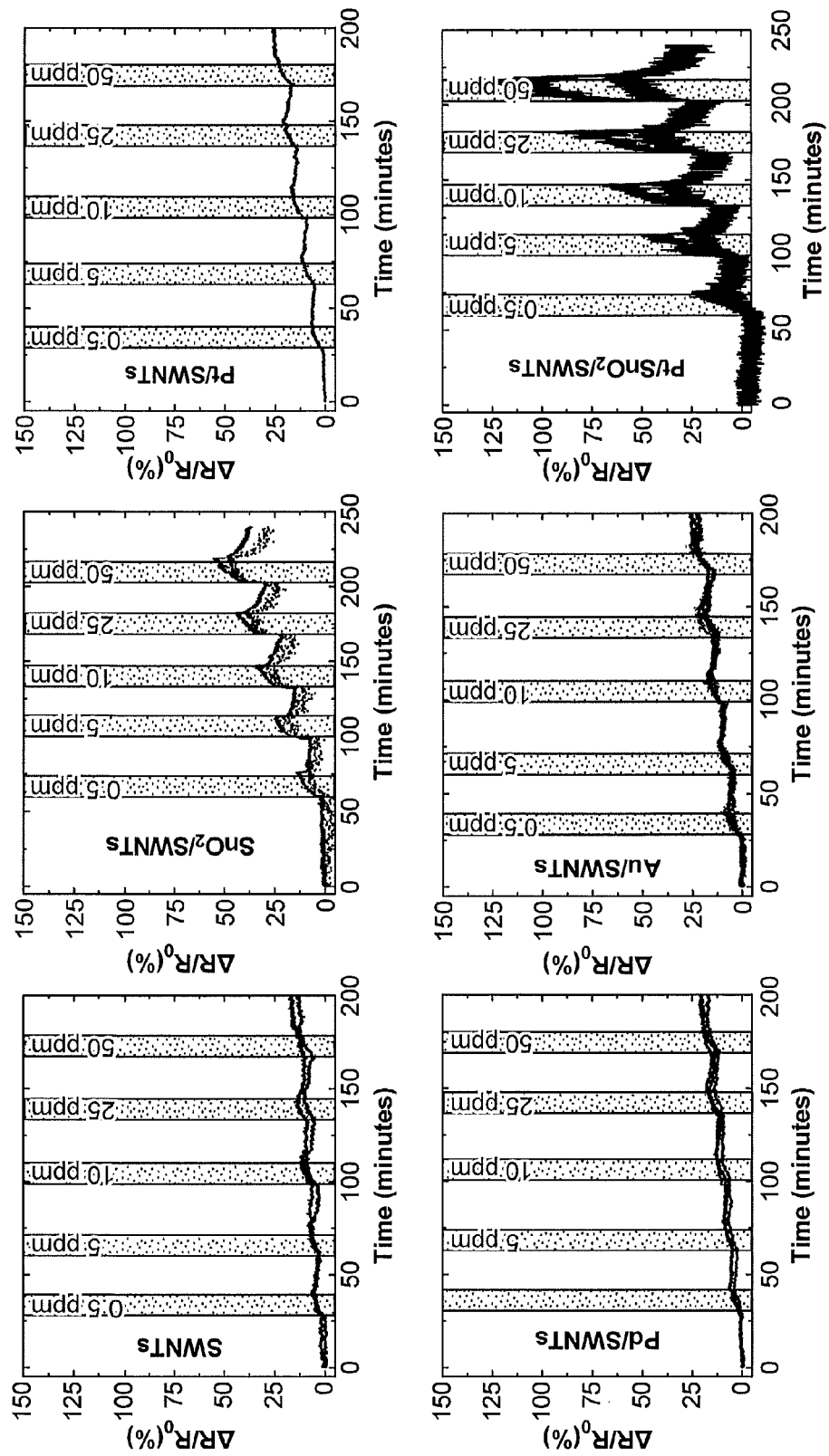
FIG. 10 is a sensor array response to different concentrations of $NH_3$.
Figure 10:
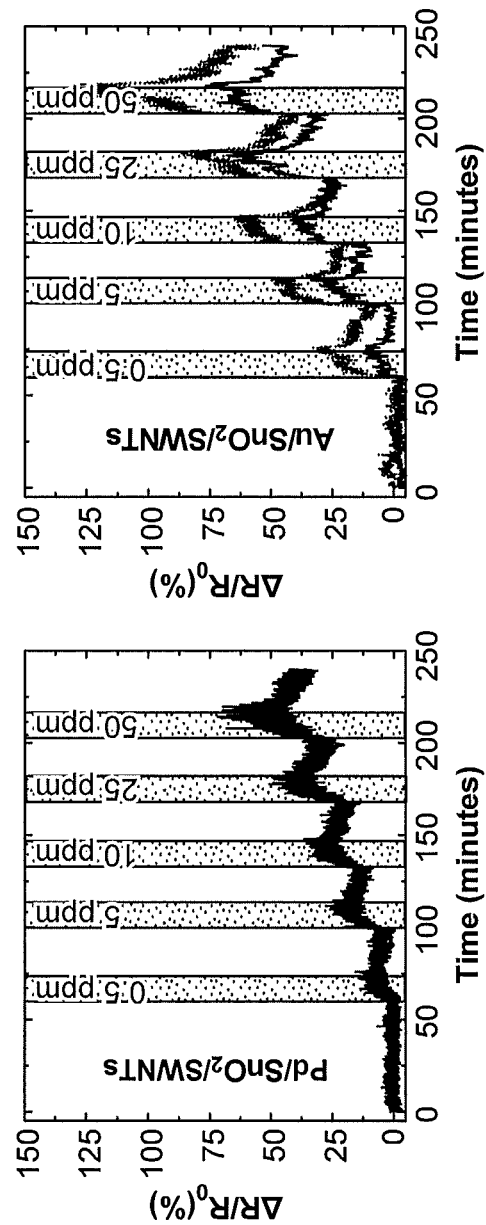
Figure 11:
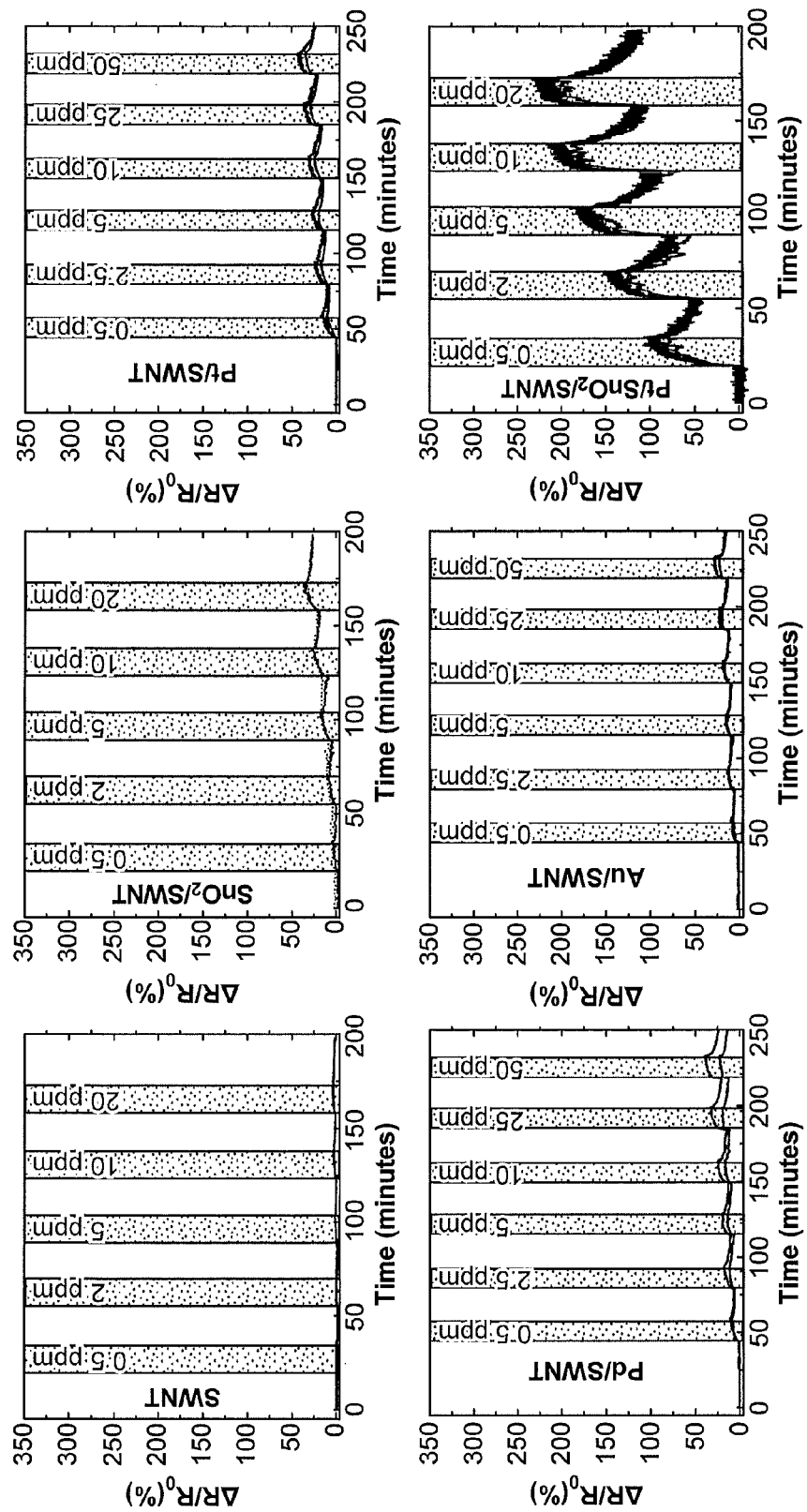
FIG. 11 is sensor array response to different concentrations of $H_2S$.
Figure 11:
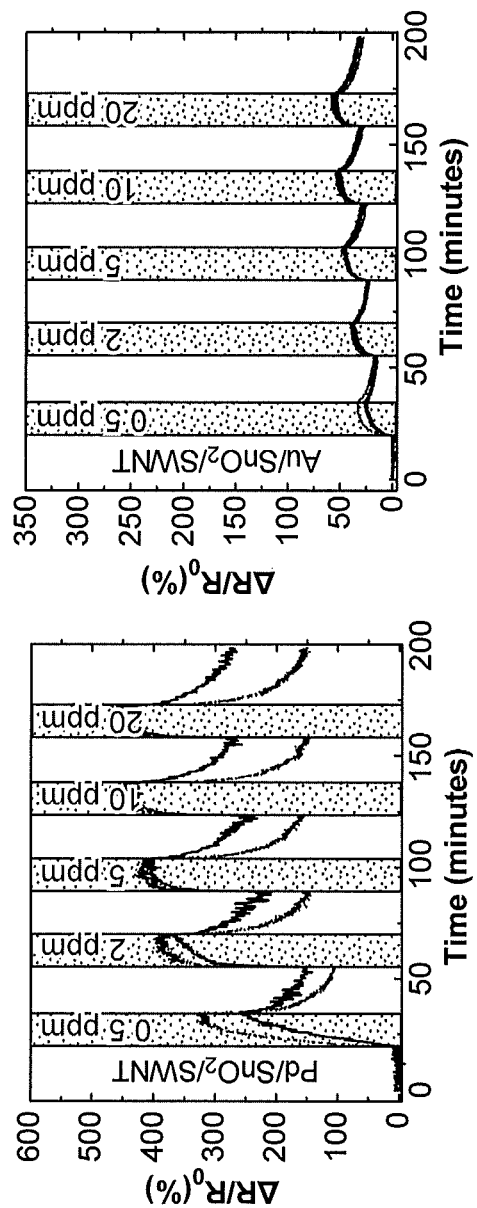
Figure 12:
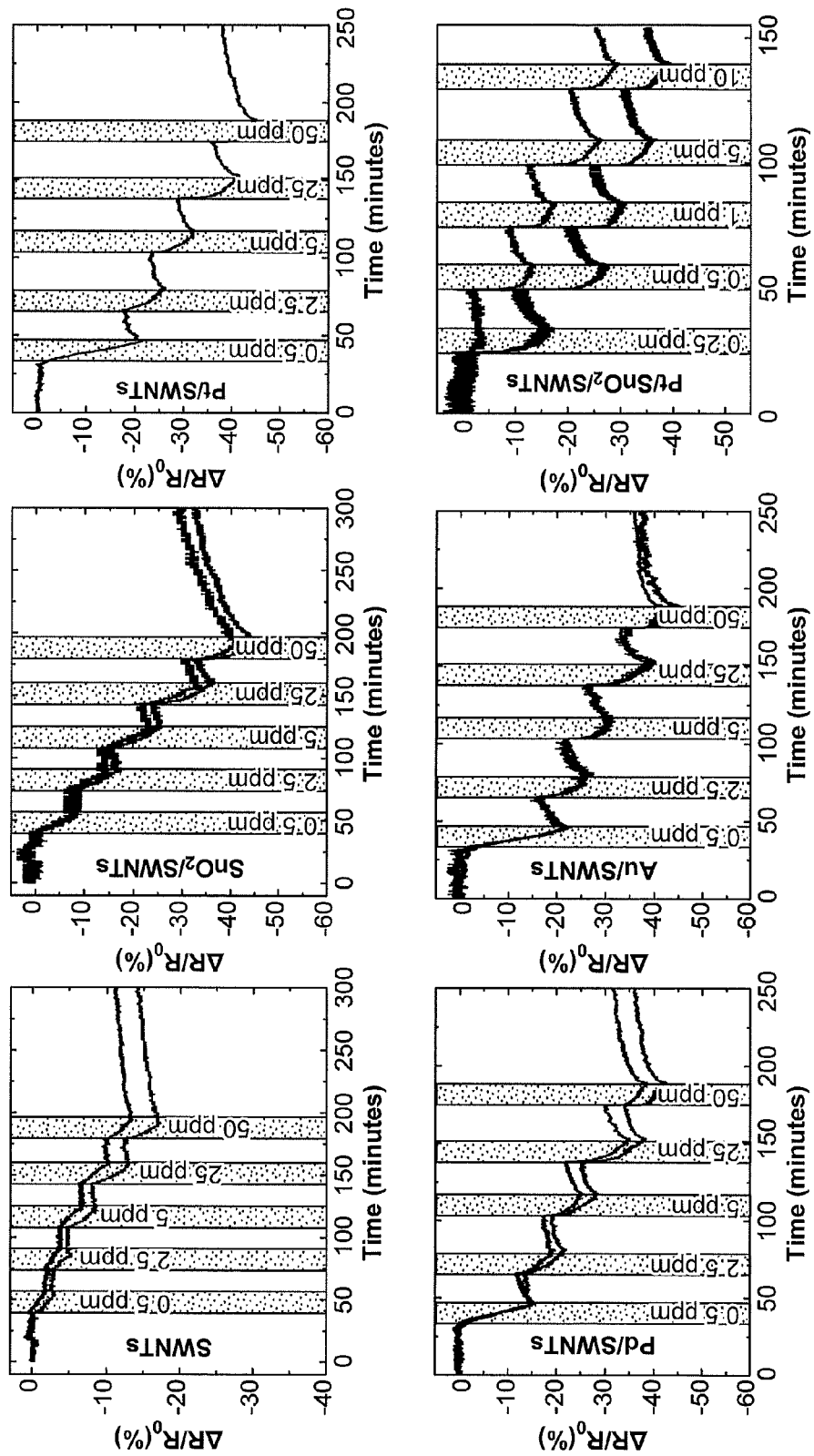
FIG. 12 is a sensor array response to different concentrations of $NO_2$.
Figure 12:
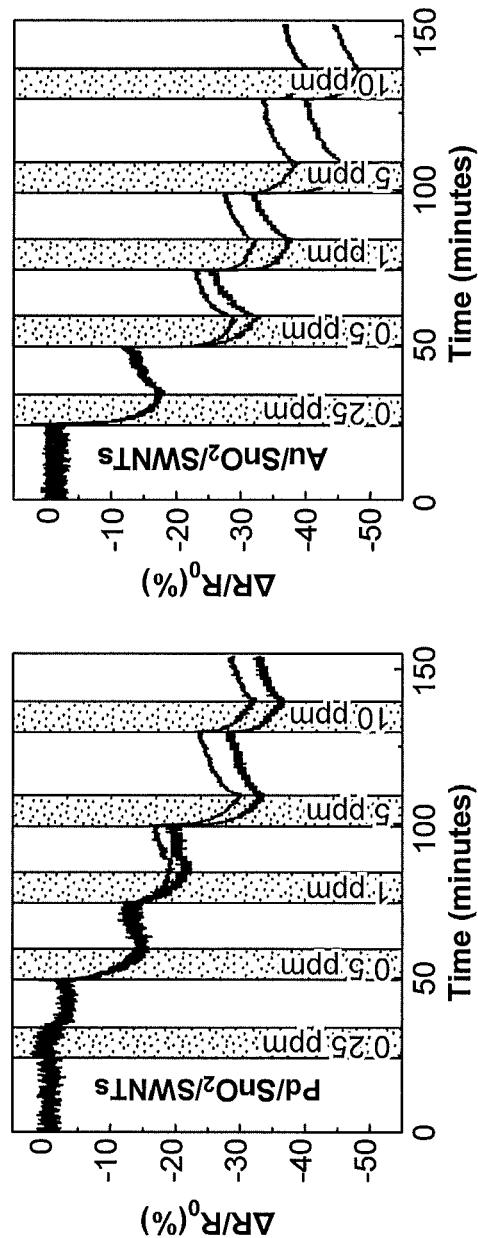
Figure 13:
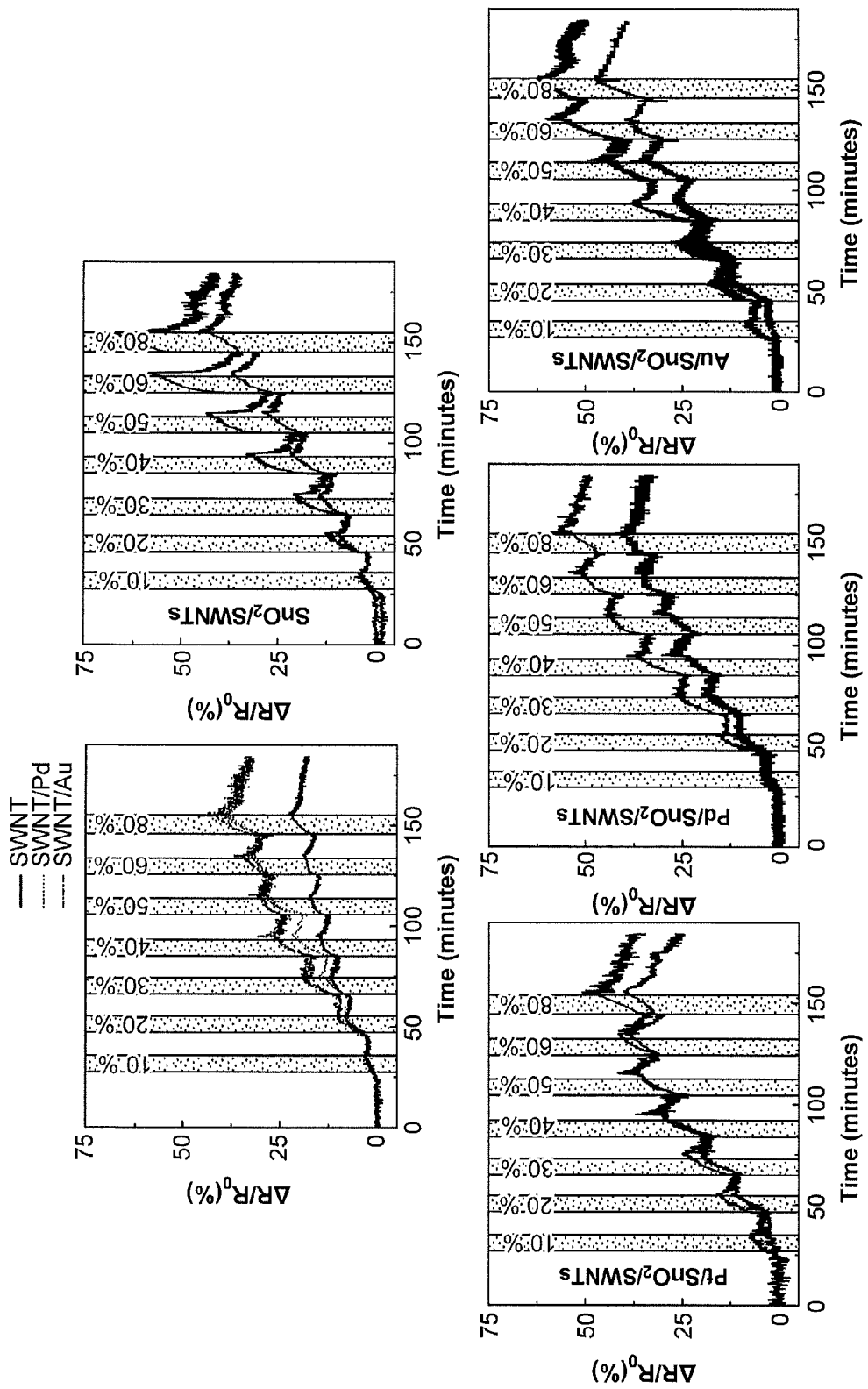
FIG. 13 is a sensor array response to different percentages of water vapor.

Construction of Nano Sensor Array:

In accordance with an exemplary embodiment, a novel hybrid chemical sensor array composed of aligned carboxylated SWNTs network, metal nanoparticle (Pd, Pt and Au) decorated SWNT network, tin oxide decorated SWNT network, metal catalyst (Pd, Pt and Au) impregnated $SnO_2$-SWNT network was fabricated. A key feature of this approach was using electrodeposition for fabricating all the sensor elements in one single chip. FIG. 9 shows an optical image of the sensor chip used and SEM images of all the sensor elements employed. For Pt and Au decoration on $SnO_2$/SWNT hybrid structure a deposition potential of −1.0 V vs. Ag/AgCl wire was used for a constant charge of 5 µC.

The eight element sensor array was then exposed to different analytes such as $NH_3$, $NO_2$, $H_2S$ and water vapor at different concentrations. FIGS. 10-13 show real-time gas sensing performance of different elements towards different analytes.

Figure 14:
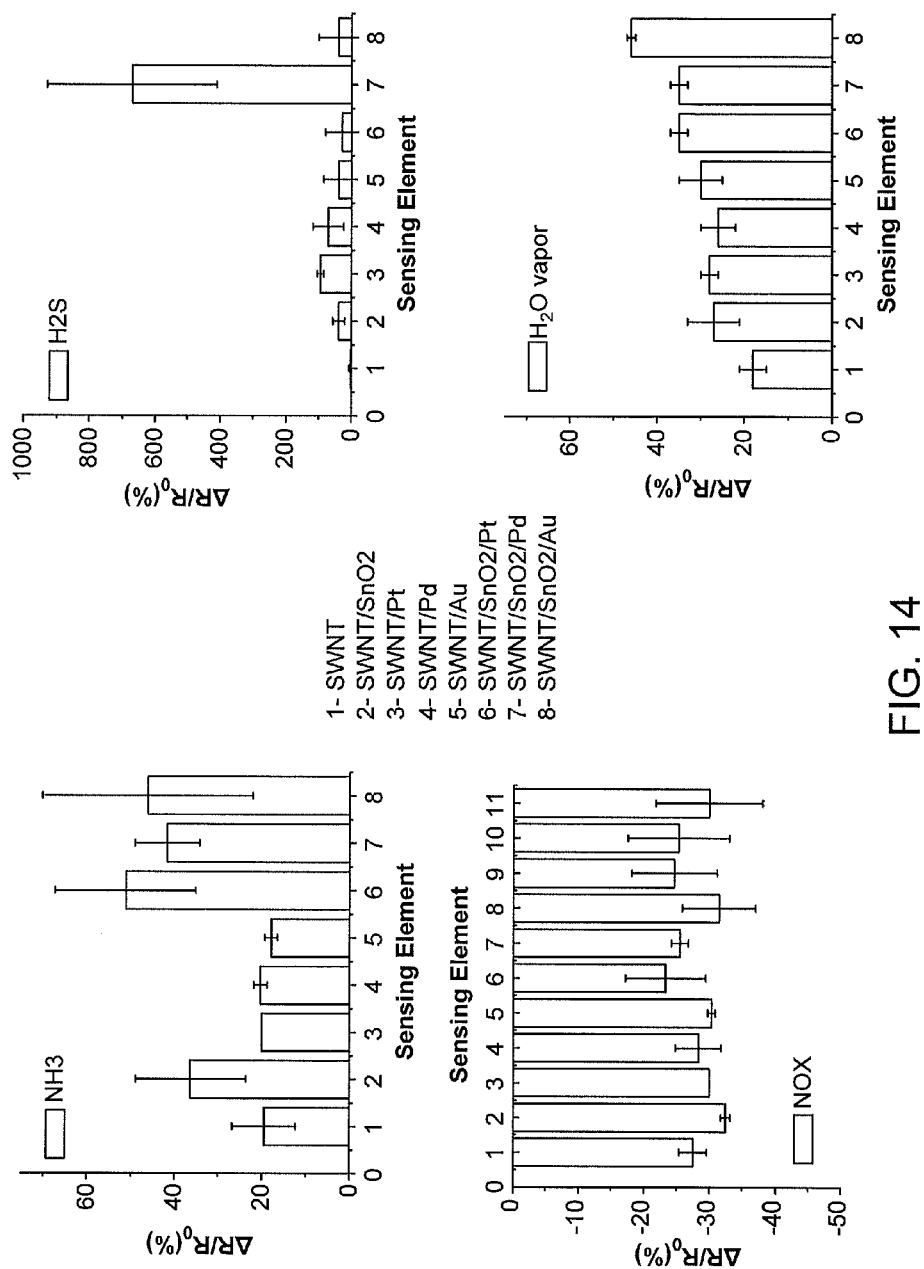
FIG. 14 is a histogram showing response of each gas sensor element to PEL concentration of $NH_3$ (25 ppm), $NO_2$ (5 ppm), $H_2S$ (20 ppm) and 50% of relative humidity.

The histogram in FIG. 14 summarizes the sensing response of the tested gases at PEL level. The height of the each bar indicates the sensor response in percentage for different analytes. In accordance with an exemplary embodiment, the catalyst embedded $SnO_2$-SWNT ternary nanostructures shows enhanced sensing performance towards $NH_3$ and $H_2S$, with a clear selectivity observed for Pd/$SnO_2$/SWNT for $H_2S$ gas sensing.

CONCLUSIONS

In accordance with an exemplary embodiment, a simple and facile yet powerful method for fabrication of hetero-nanostructures and its application towards gas sensing is disclosed herein. A sequential electrochemical templating approach was used to functionalize SWNTs with tin oxide nanocrystallites, followed by electrodeposition of metal nanoparticles. Electrical and sensing characterization was used for understanding the effect of palladium surface functionalization on $SnO_2$/SWNT hybrid nanostructures. The palladium decorated SWNT device showed high selectivity towards $H_2S$ gas with a sensor performance of 600% observed for 5 ppm concentration. The dramatic enhancement in sensing performance observed for Pd decorated $SnO_2$/SWNT samples was attributed to the dual role of Pd metal, which served as both catalytic activator and as Schottky barrier modulator. Additionally by further controlling the amount of loading and the size and growth of nanoparticles, one can envision the use of such compound nanoarchitectures for tailored gas sensing applications.

Finally, combined with the already demonstrated ability to make metal and metal oxide functionalized SWNTs, the fabrication of a high-density gas sensor nanoarrays can be facilitated. The sensor responses obtained for different analytes using different sensor recognition elements can permit subsequent pattern recognition and multi-component analysis in near future.

It will be understood that the foregoing description is of the preferred embodiments, and is, therefore, merely representative of the article and methods of manufacturing the same. It can be appreciated that many variations and modifications of the different embodiments in light of the above teachings will be readily apparent to those skilled in the art. Accordingly, the exemplary embodiments, as well as alternative embodiments, may be made without departing from the spirit and scope of the articles and methods as set forth in the attached claims.

What is claimed is:

1. A method of co-functionalizing single-walled carbon nanotube interconnects for gas sensors, the method comprising:
    fabricating by alignment single-walled carbon nanotube interconnects;
    synthesizing discrete tin oxide nanocrystallites onto a surface of the single-walled carbon nanotube interconnects by electrodeposition; and
    synthesizing metal nanoparticles onto the discrete tin oxide nanocrystallites and the surface of the single-walled carbon nanotube interconnects by electrodeposition, and
    wherein an overall sensitivity of the gas sensor is enhanced compared to other single-walled carbon nanotube gas sensors.

2. The method of claim 1, comprising:
    fabricating the single-walled carbon nanotube interconnects across a gap between a pair of electrodes.

3. The method of claim 2, further comprising:
controlling the number of single-walled carbon nanotube interconnects by adjusting a concentration of single-walled carbon nanotube in a solution.

4. The method of claim 2, further comprising:
controlling the number of single-walled carbon nanotube interconnects by adjusting an alignment time.

5. The method of claim 3, wherein the aligning of the single-walled carbon nanotube interconnects comprises:
an AC dielectrophoresis process.

6. The method of claim 1, wherein the tin oxide nanocrystallites are synthesized onto the single-walled carbon nanotube interconnects from an electrolyte solution comprised of $NaNO_3$, $HNO_3$, $SnCl_2.5H_2O$ and/or other tin ion precursors.

7. The method of claim 1, wherein the metal nanoparticles are palladium (Pd).

8. The method of claim 1, wherein the metal nanoparticles are platinum (Pt).

9. The method of claim 1, wherein the metal nanoparticles are gold (Au).

10. The method of claim 1, further comprising:
fabricating a plurality of said co-functionalizing single-walled carbon nanotube interconnects, which form a plurality of gas sensors, and wherein the plurality of gas sensors are wire-bonded and each sensor is connected in series with a load resistor.

11. The method of claim 1, wherein the gas sensors are co-functionalized for sensing at room temperature.

12. A method of co-functionalizing single-walled carbon nanotube interconnects for gas sensors, the method comprising:
fabricating by alignment single-walled carbon nanotube interconnects across a gap between a pair of electrodes;
templating discrete tin oxide nanocrystallites onto a surface of the single-walled carbon nanotube interconnects by electrodeposition; and
depositing metal nanoparticles onto the discrete tin oxide nanocrystallites and the surface of the single-walled carbon nanotube interconnects by electrodeposition, and
wherein an overall sensitivity of the gas sensor is enhanced compared to other single-walled carbon nanotube gas sensors.

13. The method of claim 12, further comprising:
controlling the number of single-walled carbon nanotube interconnects by adjusting a concentration of single-walled carbon nanotube in a solution.

14. The method of claim 12, further comprising:
controlling the number of single-walled carbon nanotube interconnects by adjusting an alignment time.

15. The method of claim 14, wherein the aligning of the single-walled carbon nanotube interconnects comprises:
an AC dielectrophoresis process.

16. The method of claim 12, comprising:
an electrolyte solution comprised of $NaNO_3$, $HNO_3$, $SnCl_2.5H_2O$ and/or other tin ion precursors which is templated onto the single-walled carbon nanotube interconnects as the discrete tin oxide nanocrystallites.

17. The method of claim 12, wherein the metal nanoparticles are palladium (Pd).

18. The method of claim 12, wherein the metal nanoparticles are platinum (Pt).

19. The method of claim 12, wherein the metal nanoparticles are gold (Au).

20. The method of claim 12, further comprising:
fabricating a plurality of said co-functionalizing single-walled carbon nanotube interconnects, which form a plurality of gas sensors, and wherein the plurality of gas sensors are wire-bonded and each sensor is connected in series with a load resistor.

21. The method of claim 12, wherein the gas sensors are co-functionalized for sensing at room temperature.

\* \* \* \* \*